US009891161B2

(12) United States Patent
Hedtke et al.

(10) Patent No.: US 9,891,161 B2
(45) Date of Patent: Feb. 13, 2018

(54) CORROSION RATE MEASUREMENT

(71) Applicant: Rosemount Inc., Shakopee, MN (US)

(72) Inventors: Robert C. Hedtke, Young America, MN (US); Fred C. Sittler, Excelsior, MN (US); Charles R. Willcox, Chanhassen, MN (US)

(73) Assignee: Rosemount Inc., Shakopee, MN (US)

( * ) Notice: Subject to any disclaimer, the term of this patent is extended or adjusted under 35 U.S.C. 154(b) by 208 days.

(21) Appl. No.: 14/656,850

(22) Filed: Mar. 13, 2015

(65) Prior Publication Data
US 2015/0260633 A1  Sep. 17, 2015

Related U.S. Application Data

(60) Provisional application No. 61/953,173, filed on Mar. 14, 2014.

(51) Int. Cl.
*G01L 1/04* (2006.01)
*G01N 17/04* (2006.01)
*G01L 9/00* (2006.01)
*G01L 13/02* (2006.01)
*G01L 19/06* (2006.01)

(52) U.S. Cl.
CPC .......... *G01N 17/043* (2013.01); *G01L 9/0072* (2013.01); *G01L 13/025* (2013.01); *G01L 19/0645* (2013.01); *G01N 17/04* (2013.01)

(58) Field of Classification Search
USPC .................................................. 73/862.637
See application file for complete search history.

(56) References Cited

U.S. PATENT DOCUMENTS

| | | | |
|---|---|---|---|
| 2,976,123 A | 3/1961 | Marsh et al. | .................... 23/253 |
| 4,046,010 A * | 9/1977 | Akeley | ................... G01L 9/007 29/454 |
| 4,468,613 A | 8/1984 | Slough et al. | ................ 324/71.2 |

(Continued)

FOREIGN PATENT DOCUMENTS

| | | |
|---|---|---|
| CN | 1225733 | 8/1999 |
| CN | 1338043 | 2/2002 |

(Continued)

OTHER PUBLICATIONS

Notification of Transmittal of the International Search Report and the Written Opinion of the International Searching Authority from PCT/US2015/047905, dated Nov. 5, 2015.

(Continued)

*Primary Examiner* — Eric S McCall
*Assistant Examiner* — Mohammed E Keramet-Amircolai
(74) *Attorney, Agent, or Firm* — Westman, Champlin & Koehler, P.A.

(57) ABSTRACT

A corrosion rate measurement system includes a first membrane of a first material configured to be exposed to a corrosive material and deflect in response to corrosion. A second membrane is configured to be exposed to a corrosive material and deflect in response to corrosion. A pressure sensor is operably coupled to at least one of the first and second membranes and configured to measure deflection of at least one of the first and second membranes as a function of a pressure and an amount of corrosion at least one of the first and second membranes.

23 Claims, 9 Drawing Sheets

(56) References Cited

U.S. PATENT DOCUMENTS

| | | | |
|---|---|---|---|
| 4,506,540 A | 3/1985 | Marsh | 73/29 |
| 5,061,846 A | 10/1991 | Gergely | 250/227.14 |
| 5,092,177 A | 3/1992 | Varacca | 73/708 |
| 5,127,433 A | 7/1992 | Argyle et al. | 137/559 |
| 5,253,674 A | 10/1993 | Argyle et al. | 137/559 |
| 5,301,001 A | 4/1994 | Murphy et al. | 356/35.5 |
| 5,447,073 A | 9/1995 | Kalinoski | 73/861.24 |
| 5,571,955 A | 11/1996 | Beavers et al. | 73/86 |
| 5,659,128 A | 8/1997 | Goldenberg | |
| 5,683,594 A | 11/1997 | Hocker et al. | 216/33 |
| 5,731,523 A | 3/1998 | Cusumano et al. | 73/783 |
| 5,854,557 A | 12/1998 | Tiefnig | 324/700 |
| 5,948,971 A | 9/1999 | Brooker et al. | |
| 6,079,276 A * | 6/2000 | Frick | G01L 9/0075 361/283.4 |
| 6,280,603 B1 | 8/2001 | Jovancicevic | 205/775.5 |
| 6,294,133 B1 | 9/2001 | Sawada et al. | 422/82.01 |
| 6,341,185 B1 | 1/2002 | Elster et al. | 385/12 |
| 6,383,451 B1 * | 5/2002 | Kim | G01N 17/04 324/71.1 |
| 6,426,796 B1 | 7/2002 | Pulliam et al. | 356/501 |
| 6,451,212 B2 | 9/2002 | Iseri et al. | 210/746 |
| 6,487,895 B2 | 12/2002 | Brooker et al. | |
| 6,571,639 B1 | 6/2003 | May et al. | 73/800 |
| 6,671,055 B1 | 12/2003 | Wavering et al. | 356/478 |
| 6,931,937 B1 | 8/2005 | Tanaka et al. | 73/753 |
| 7,024,918 B2 | 4/2006 | Bell et al. | 73/37 |
| 7,131,335 B2 | 11/2006 | Textor | 73/716 |
| 7,131,337 B2 | 11/2006 | Kato et al. | 73/754 |
| 7,290,450 B2 | 11/2007 | Brown et al. | 73/579 |
| 7,295,131 B2 | 11/2007 | Anderson et al. | 340/679 |
| 7,437,939 B1 | 10/2008 | Chakroborty et al. | |
| 7,540,197 B2 | 6/2009 | Wavering et al. | 73/715 |
| 7,866,211 B2 | 1/2011 | Brown | 73/579 |
| 2003/0006148 A1 | 1/2003 | Nielsen et al. | 205/775.5 |
| 2004/0055391 A1 | 3/2004 | Douglas et al. | 73/779 |
| 2005/0011278 A1 | 1/2005 | Brown | |
| 2005/0122121 A1 | 6/2005 | Gilboe | 324/700 |
| 2005/0150279 A1 * | 7/2005 | Taber | G01N 17/04 73/86 |
| 2005/0151546 A1 | 7/2005 | Taber | 324/700 |
| 2006/0016265 A1 | 1/2006 | Kaneko et al. | 73/715 |
| 2006/0162431 A1 * | 7/2006 | Harris | G01N 17/043 73/86 |
| 2006/0217902 A1 | 9/2006 | Bernard et al. | 702/47 |
| 2006/0260409 A1 | 11/2006 | Yane et al. | 73/715 |
| 2007/0019898 A1 | 1/2007 | Chimenti et al. | 385/12 |
| 2007/0074563 A1 | 4/2007 | Liu et al. | 73/54.24 |
| 2007/0120572 A1 | 5/2007 | Chen et al. | 324/700 |
| 2007/0199379 A1 | 8/2007 | Wolf et al. | 73/590 |
| 2007/0227252 A1 | 10/2007 | Leitko et al. | 73/717 |
| 2008/0141780 A1 * | 6/2008 | Wavering | G01N 17/04 73/723 |
| 2008/0253058 A1 | 10/2008 | Chakroborty et al. | |
| 2010/0064816 A1 | 3/2010 | Filippi et al. | |
| 2015/0177033 A1 | 6/2015 | Clarke | |
| 2015/0260633 A1 | 9/2015 | Hedtke et al. | |
| 2016/0091411 A1 | 3/2016 | Hedtke | |
| 2016/0363525 A1 | 12/2016 | Friedersdorf | |

FOREIGN PATENT DOCUMENTS

| | | |
|---|---|---|
| CN | 1347496 | 5/2002 |
| CN | 1651883 | 8/2005 |
| CN | 1651886 | 8/2005 |
| CN | 1657893 | 8/2005 |
| CN | 1699191 | 11/2005 |
| CN | 1784589 | 6/2006 |
| CN | 201218797 | 4/2009 |
| EP | 0 240 236 | 10/1987 |
| EP | 0 971 214 | 1/2000 |
| EP | 0 984 252 | 3/2000 |
| EP | 2 124 034 | 11/2009 |
| JP | 53-065783 | 6/1978 |
| JP | 56-24510 | 3/1981 |
| JP | 61-177783 | 8/1986 |
| JP | 3-183946 | 8/1991 |
| JP | 2000-131174 | 5/2000 |
| JP | 2000-171386 | 6/2000 |
| JP | 2000-266662 | 9/2000 |
| JP | 2001-4527 | 1/2001 |
| JP | 2002-277339 | 9/2002 |
| JP | 2007-021996 | 2/2007 |
| JP | 2008-261652 | 10/2008 |
| JP | 2009-250110 | 10/2009 |
| JP | 2010-523999 | 7/2010 |
| JP | 2012-093175 | 5/2012 |
| WO | WO 2002/16908 | 2/2002 |
| WO | WO 2006/065770 | 6/2006 |
| WO | WO 2009/016594 | 2/2009 |

OTHER PUBLICATIONS

Notification of Transmittal of the International Search Report and the Written Opinion of the International Searching Authority from PCT/US2015/020354, dated Jun. 2, 2015.
Office Action from Chinese Patent Application No. 201520148367.8, dated May 19, 2015.
Brochure entitled "CorrTran® MV Corrosion Monitoring Transmitter", by Pepperl+Fuchs, pp. 1-61, Mar. 2012.
Device Measurement and Maintenance, Issue 9, 1997, pp. 38-41.
Device Management and Maintenance, Issue 10, 1997, pp. 35-38.
Corrosion Test Methods and Monitoring Technology, Edition 1, May 2007, 9 pages.
1000 Examples of Water Disposal Anti-Corrosion and Invalidation Analysis, Sep. 2000, 4 pages.
Metal Corrosion Theory and Application, Dec. 1984, pp. 337-341.
Notification of Transmittal of the International Search Report and the Written Opinion of the International Search Authority from PCT/US2016/032020, dated Sep. 23, 2016.
Examination Report from Australian Patent Application No. 2015229218, dated Feb. 1, 2017.
European Communication from European Patent Application No. 15714072.4, dated Oct. 21, 2016.
Office Action from Chinese Patent Application No. 201510114343.5, dated Feb. 28, 2017.
Examination Report from Australian Patent Application No. 2015229218, dated Aug. 4, 2017.
Communication from European Patent Application No. 15714072.4, dated Jun. 26, 2017.
Office Action from Canadian Patent Application No. 2,941,012, dated Jun. 6, 2017.
Communication from European Patent Application No. 15763727.3, dated May 10, 2017.
Office Action from Japanese Patent Application No. 2016-557291, dated Aug. 23, 2017.
Office Action from European Patent Application No. 15714072.4, dated Oct. 31, 2017.
Office Action from Chinese Patent Application No. 201510114343.5, dated Oct. 31, 2017.

* cited by examiner

CORROSION RATE MEASUREMENT

CROSS-REFERENCE TO RELATED APPLICATION

The present application is based on and claims the benefit of U.S. provisional patent application Ser. No. 61/953,173, filed Mar. 14, 2014, the content of which is hereby incorporated by reference in its entirety.

BACKGROUND

The present invention relates to corrosion of components in various settings. More specifically, the present invention relates to monitoring such corrosion.

Corrosion is the gradual destruction of materials by chemical or other reaction with its environment. Corrosion degrades the useful properties of materials and structures including strength, appearance, and permeability to fluids. Many structural alloys corrode merely from exposure to moisture in air but the process can be strongly affected by exposure to certain substances. Corrosion can be concentrated locally to form a pit or crack, or it can extend across a wide area uniformly corroding the surface.

The field of corrosion measurement, control, and prevention is very broad. Corrosion measurement employs a variety of techniques to determine how corrosive the environment is and at what rate metal loss is being experienced. Some corrosion measurement techniques can be used on-line, constantly exposed to the process stream, while others provide off-line measurement, determined in a laboratory analysis. Some techniques give a direct measure of metal loss or corrosion rate while others are used to infer that a corrosive environment may exist.

The rate of corrosion dictates how long any process plant can be usefully and safely operated. The measurement of corrosion and the action to remedy high corrosion rates permits the most cost effective plant operation to be achieved while reducing the life-cycle costs associated with the operation.

The following list details the most common corrosion monitoring techniques which are used in industrial applications. Corrosion coupons, ER, and LPR form the core of industrial corrosion monitoring systems and will be explained in further detail.

- Corrosion Coupons (weight loss measurements)
- Electrical Resistance (ER)
- Linear Polarization Resistance (LPR)
- Galvanic (ZRA) I Potential
- Hydrogen Penetration
- Microbial
- Sand/Erosion The weight loss technique is the best known and simplest corrosion monitoring technique. The method involves exposing a specimen of material (coupon) to a process environment for a given duration, then removing the specimen for analysis. The basic measurement which is determined from corrosion coupons is weight loss. Corrosion rate can be calculated by dividing the weight loss by material density, coupon surface area, and time of exposure. Coupon monitoring is most useful in environments where corrosion rates do not significantly change over long time periods. However, they can provide a useful correlation with other techniques.

ER probes can be thought of as "electronic" corrosion coupons. ER probes provide a basic measurement of metal loss and the value of metal loss can be measured at any time while the probe is in-situ. The ER technique measures the change in electrical resistance of a corroding metal element exposed to the process. The action of corrosion on the surface of the element produces a decrease in its cross-sectional area with a corresponding increase in its electrical resistance.

The LPR technique is based on electro-chemical theory. A small voltage is applied to an electrode in solution. The current needed to maintain a specific voltage shift (typically 10 mV) is directly related to the corrosion on the surface of the electrode in the solution. By measuring the current a corrosion rate can be derived. The advantage of the LPR technique is that the measurement of corrosion rate is made instantaneously whereas with coupons or ER some period of exposure is required to determine corrosion rate. The LPR technique can only be performed in clean aqueous electrolytic environments and will not work in gases.

Corrosion is an expense in many systems. Impact of corrosion includes lost production, system down time, system failures, as well as repair time and expense. There is important need to prevent and monitor corrosion.

SUMMARY

A corrosion rate measurement system includes a first membrane of a first material configured to be exposed to a corrosive material and deflect in response to corrosion. A second membrane is configured to be exposed to a corrosive material and deflect in response to corrosion. A pressure sensor is operably coupled to at least one of the first and second membranes and configured to measure deflection of at least one of the first and second membranes as a function of a pressure and an amount of corrosion of at least one of the first and second membranes.

DETAILED DESCRIPTION OF ILLUSTRATIVE EMBODIMENTS

Figure 1:
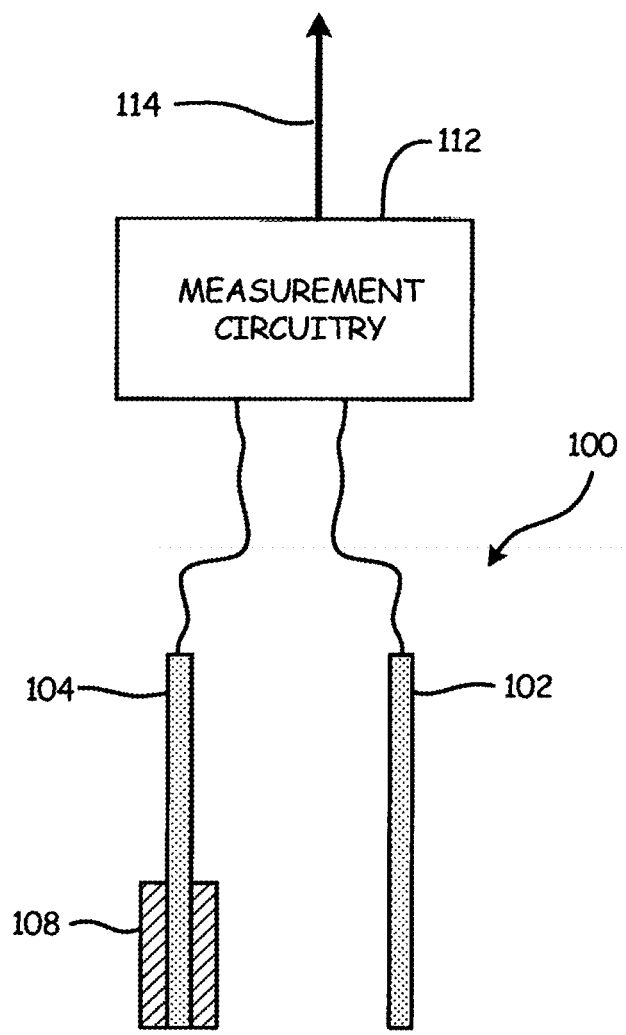
FIG. 1 is a side plan view of pressure sensors including a sacrificial coating used to measure corrosion.

Accurately measuring corrosion rates is an important customer need for safety, reliability, and efficiency. Several embodiments will be described. All embodiments include some type of pressure sensor and in most cases a differential pressure sensor. The basic concept will work with most any differential sensor technology. Typically an oil filled differential pressure sensor system is oil filled under a low back pressure, for example a few psi. Most embodiments described herein use a differential pressure sensor system that is oil filled under an internal-high back pressure, for example 500 to 1000 psi. One advantage of a high back pressure oil fill is to allow corrosion measurement largely independent of process pressure, even zero process pressure. Additionally, the high and low side membranes of the differential pressure sensor are always placed at the same location in the process. Therefore, the external differential process pressure is always zero. One embodiment is based on an oil filled differential capacitance sensor that is sealed under a high back pressure. A sacrificial isolation membrane on one side will lose material due to corrosion which changes its stiffness. A thicker reference isolation membrane on the other side will also lose material but its stiffness will change less. The sensor system responds by balancing the internal forces to zero which in turn moves a center diaphragm of a capacitance based pressure sensor. Measuring the sensor capacitance change effectively measures the corrosion rate. Another embodiment utilizes two absolute or gauge pressure sensors, each monitoring the back-pressure behind two independent isolator membranes. One membrane, for example, could be a sacrificial membrane, while the other could serve as a reference membrane having different corroding properties than the sacrificial membrane. By tracking the back-pressure change between the two sides, a determination of the corrosion rate of the sacrificial membrane can be determined.

Many operators currently inspect for corrosion during scheduled repair and maintenance at either fixed or unplanned intervals. New technologies are enabling monitoring corrosion in real time using the plant control and automation system. This allows the assessment of corrosion in shorter time intervals with the ability to control and mitigate the rate of damage.

By integrating corrosion measurements into automation systems, corrosion monitoring is easier to implement, automate, and view with other process variables. This approach is more cost-effective than conventional stand-alone systems, requires less manual labor, provides a greater degree of integration with systems to record, control, and optimize.

It is desirable for plant operators to increase efficiency and productivity by even small amounts. However, corrosion costs are one of the few areas in plant operations where large improvements are possible along with associated cost-reduction. Corrosion measurement can be considered a primary variable that is subject to control and optimization in the process.

Pursuant to one embodiment, FIG. 1 is a side plane view drawing of a corrosion measurement sensor or system 100 based on two absolute sapphire capacitance pressure sensors 102, 104. Sensor 102 is configured as the reference sensor. It is designed to be substantially immune to the specific corrosive agents of interest. It may be an unprotected sapphire sensor or a coated sensor. Sensor 104 is configured as the sacrificial sensor. Sensor 104 itself is immune to corrosion but the sensor is covered with a sacrificial coating 108 that is susceptible to the specific corrosive agents. The sensors 102, 104 may be of any appropriate configuration. One example configuration is shown in U.S. Pat. No. 6,079,276, issued Jun. 27, 2000, to Frick et al.

The coating 108 acts as a membrane and is a relatively stiff member. For example, if the process pressure is 500 psi, the reference sensor 102 would indicate 500 psi while the sacrificial sensor 108 may indicate only 10 psi. As the sacrificial coating 108 corrodes and becomes thinner, the sacrificial sensor 104 will indicate increasing pressure. An oil-less system 100 is shown which subjects all materials, including a mixed metal brazing which is used to mount the sensors 102, 104 to a housing (not shown in FIG. 1) to the corrosive process. Sapphire is extremely stiff so the sacrificial coating 108 should be very thick. The system 100 can also provide process pressure from the reference sensor but the signal of interest is the difference between the two measured pressures which is a measure of corrosion. This system 100 requires process pressure to generate signals.

FIG. 1 also illustrates measurement circuitry 112 which electrically couples to sensors 102 and 104. Measurement circuitry 112 is configured to determine a difference in the outputs from the two sensors 102, 104. For example, a difference in the electrical capacitance of sensors 102, 104. This is related to a difference in the pressure being sensed by each sensor 102, 104. This pressure difference can be related to the amount of corrosion of the sacrificial coating 108 as discussed above. An output 114 is provided related to the measured corrosion. This output can be used locally, or transmitted to a remote location using known techniques. Such techniques include transmission over a process control loop including a wireless process control loop. Examples of specific types of process control loops include two-wire 4-20 mA loops, loops which communicate in accordance with the HART® communication protocol, Fieldbus protocols, as well as wireless techniques such as the WirelessHART® communication protocol in accordance with IEC 62591 Standard, among others.

Figure 2:
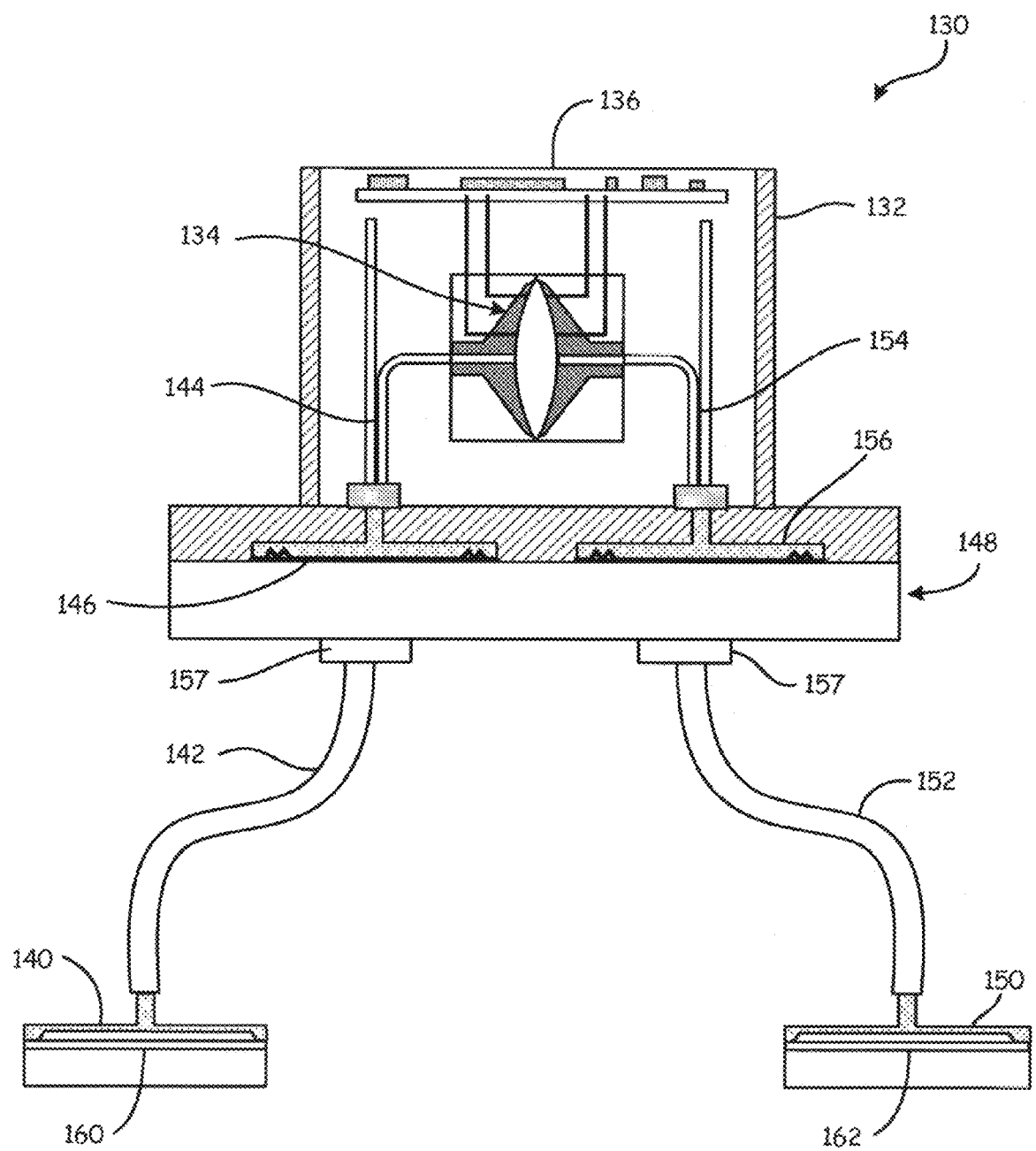
FIG. 2 is a simplified cross sectional view of a differential pressure transmitter coupled to remote seals for measuring corrosion.

Pursuant to another embodiment, FIG. 2 is a side cross-sectional view of a pressure transmitter 132 configured as a corrosion sensor or measurement system 130. Transmitter 132 includes a differential pressure sensor 134 having electrical outputs coupled to measurement circuitry 136. The differential pressure sensor 134 illustrated in FIG. 2 includes a diaphragm 159 (not shown in FIG. 2) which responsively deflects based upon balancing the internal pressure between the two sides. Pressure sensor 134 couples to a first remote seal 140 through capillary tubes 142 and 144. Tubes 142 and 144 may be filled with, for example, an isolation fill fluid under back pressure. Transmitter 132 includes an isolation diaphragm 146 which couples to a stainless steel flange 148. A second remote seal 150 is fluidically coupled to pressure sensor 134 through capillary tubes 152, 154 and isolation diaphragm 156. Capillary tubes 142, 152 are welded to flange 148 at weld points 157. Remote seals 140, 150 each include respective pressure sensitive membranes 160, 162 which are exposed to a corrosive process fluid. The membranes 160 and 162 are configured to deflect in response to an applied pressure that could be external or internal. The amount of deflection of membranes 160, 162 is fluidically transferred as a change in pressure through their respective capillary tubes 142, 144, 152, 154 to the differential pressure sensor 134. Differential pressure sensor 134 has an electrical characteristic such as capacitance which changes as a function of any imbalance in the applied pressures.

Membranes 160, 162 are configured such that in response to exposure to a corrosive fluid, the amount of deflection of one of the membranes, for example a sacrificial diaphragm 160, will change in a manner which is greater than a "reference" membrane 162 in response to the applied pressure that could be external or internal. This can be achieved through any appropriate technique. For example, membrane 160 may be fabricated of a material which corrodes at a faster rate than that of membrane 162. In another example configuration, membrane 162 is substantially thicker than membrane 160, but made of the same material. Other physical characteristics may be employed to achieve the desired relationship between corrosion and the sensor response to deflection based upon balancing internal pressure. For example, the surface area or diameter of the membrane(s) may be changed as desired.

The corrosion measurement system 130 illustrated in FIG. 2 may be based upon an unpressurized system and react in response to a pressure applied by the corrosive process fluid itself. As discussed above, in another example configuration, the capillary tubes 142, 144, 152 and 154 are filled under a back pressure with the oil fill fluid. In such a configuration, corrosion in a system in which the process fluid is not under pressure may be measured. Specifically, the amount by which the membrane 160 deflects in response to the applied back pressure will change as the membrane 160 corrodes.

Figure 3:
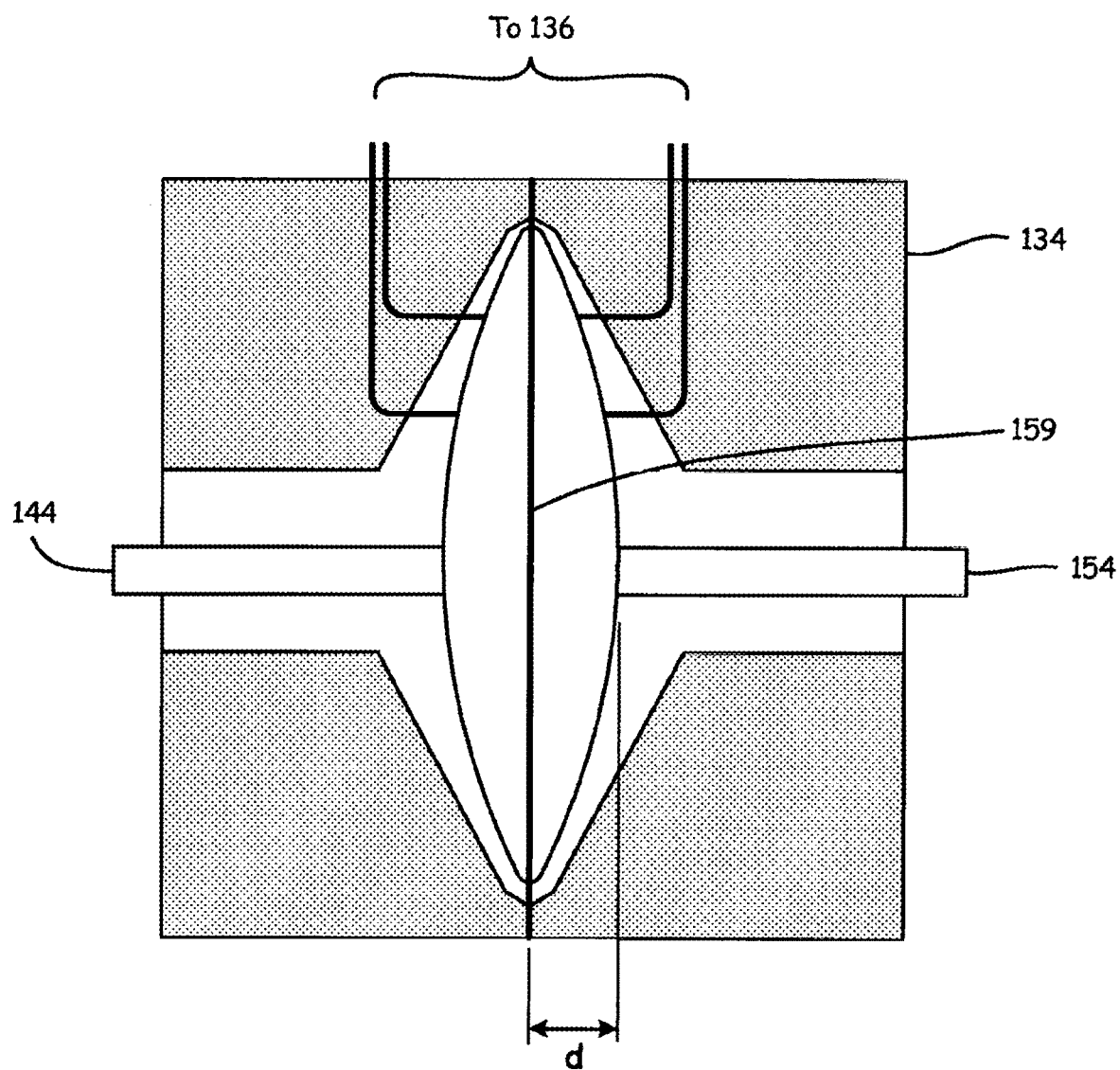
FIG. 3 is an enlarged cross sectional view of a capacitance based differential pressure sensor.

This configuration is feasible because of the extreme sensitivity of the differential sensor 134. The cavity depth (d) of the sensor is shown pictorially in FIG. 3. This depth is range dependent but is approximately 4 mils (0.004"). Assume the center diaphragm 159 movement is from 0 to URL (upper range limit) is 0.004"≈10$^{-4}$ m. The accuracy specification of a particular sensor may be 0.025% down to 10:1 range-down. Therefore, the system can resolve 0.025% of 10$^{-5}$ m=0.00025×0.00001=2.5 nm=25 angstrom of movement of the center diaphragm 159.

This calculation illustrates the sensor's precision. However, the calculation of interest is volumetric displacement of oil which would be proportional to material loss. The cavity volume change from a deflecting circular diaphragm can be approximated as one half of a cylinder=½πr$^2$h where r≈1 cm=10$^{-2}$ m and h=10$^{-5}$ m. As stated above the system can resolve 0.025% of this volume. This equals 4×10$^{-13}$ m$^3$=4×10$^{-4}$ mm$^3$. Allowances, however, should be made for other errors when making long term measurements such as temperature effects and long term stability.

Corrosion rates are often expressed in mils per year. One mil per year may be considered excellent in one application, but severe in a different application. Two key elements of the measurement are corrosion sensitivity (the smallest measurable corrosion rate limited by the resolution and stability of the capacitance sensor) and corrosion range (the maximum amount of measurable corrosion limited by the center diaphragm travel of the capacitance sensor). In general, improving one attribute comes at the expense of the other.

Modeling the design is complex because a thinning membrane creates convoluted effects. The simplified equation shown below is useful to explain the measurement capability and design trade-offs. For a sensor center diaphragm stiffness $S_C$ much smaller than the isolator stiffness $S_I$ the detected differential pressure is:

$$\delta P = -\frac{3}{2} P \left(\frac{S_C}{S_I}\right) \frac{\delta t}{t} \quad \text{EQUATION 1}$$

where P is the back (or internal) pressure, δt is the change in isolator thickness caused by corrosion, and t is the original isolator thickness. The values of $S_C$ can be determined from past modeling of the sensor and are range dependent.

The isolator stiffness $S_I$ for a clamped edge membrane is:

$$S_I = -\frac{32}{3\pi} \frac{E}{(1-v^2)} \frac{r^3}{r^6} \quad \text{EQUATION 2}$$

where E is the isolator Young's modulus having radius r, thickness t, and Poisson's constant v.

The models indicate there are some known factors based on the sacrificial isolator material and there are some variables based on design tradeoffs including back pressure, sensor range, isolator dimensions, and detectable change in thickness due to corrosion.

For example, for a 1 inch diameter, 0.05 inch thick, carbon steel sacrificial isolator connected to a typical sensor and oil filled with a back pressure of 6,000 psi, a 0.001 inch loss of isolator membrane thickness would create a 1.44 psi differential pressure, or 40 inches of water. This is ⅙ of the range 2 of 250 inches of water. Therefore for this design the corrosion range (the maximum amount of measurable corrosion) would be approximately 0.006 inches. The sensor can measure 40 inches of water to an accuracy of 0.05% or 0.02 inches of water. Therefore for this design the corrosion sensitivity (the smallest measurable corrosion rate) would be approximately 0.05%×365 days=0.18 days (about 4.4 hours) to detect an annual rate of 0.001 inches.

Figure 4:
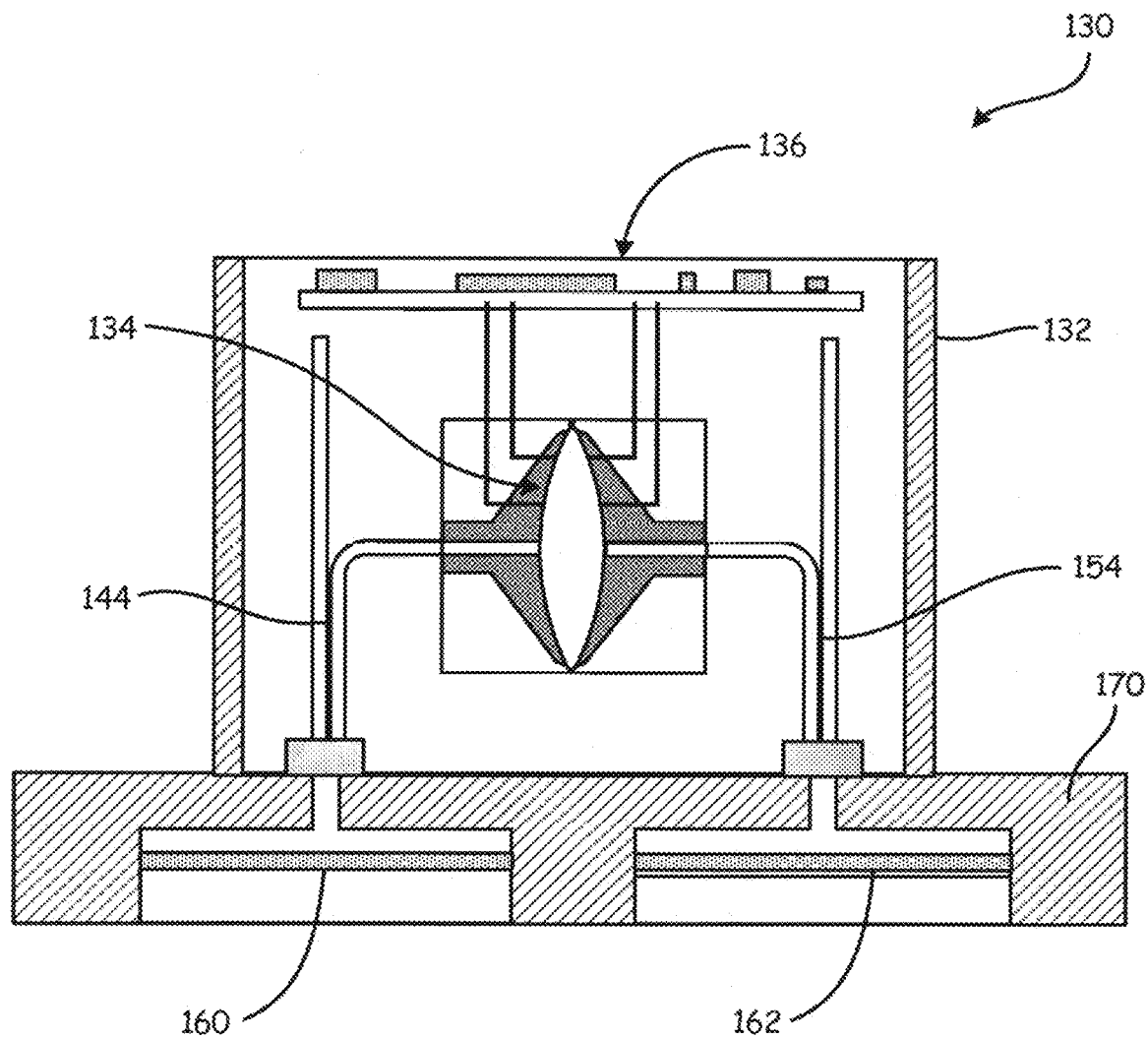
FIG. 4 is a side cross-sectional view of a differential pressure transmitter configured to measure corrosion.

FIG. 4 shows another example embodiment of a corrosion measurement system 130 using differential pressure transmitter 132. The configuration of the embodiment shown in FIG. 4 is similar to that shown in FIG. 2. However, in the configuration of FIG. 4, the corrosion sensing (sacrificial) membrane 160 and the reference membrane 162 are mounted on a flange 170 of the transmitter 132. In the configuration of FIG. 4, a standard pressure transmitter 132 may be modified to include the corrosion sensing membrane 160 and the reference membrane 162. Additionally, if there is a space between the flow of a process fluid and membrane 160, this may reduce the amount of corrosion experienced by the membrane 160. For example, if connection tubing is used to couple sacrificial membrane 160 to a flow of process fluid, the flow within the connection is relatively stagnant in comparison to the flow within the process fluid within the process itself. Thus, the sacrificial membrane 160 may corrode at a slower rate, because it is exposed to less of the corrosive process fluid than the other components within the process.

Figure 5:
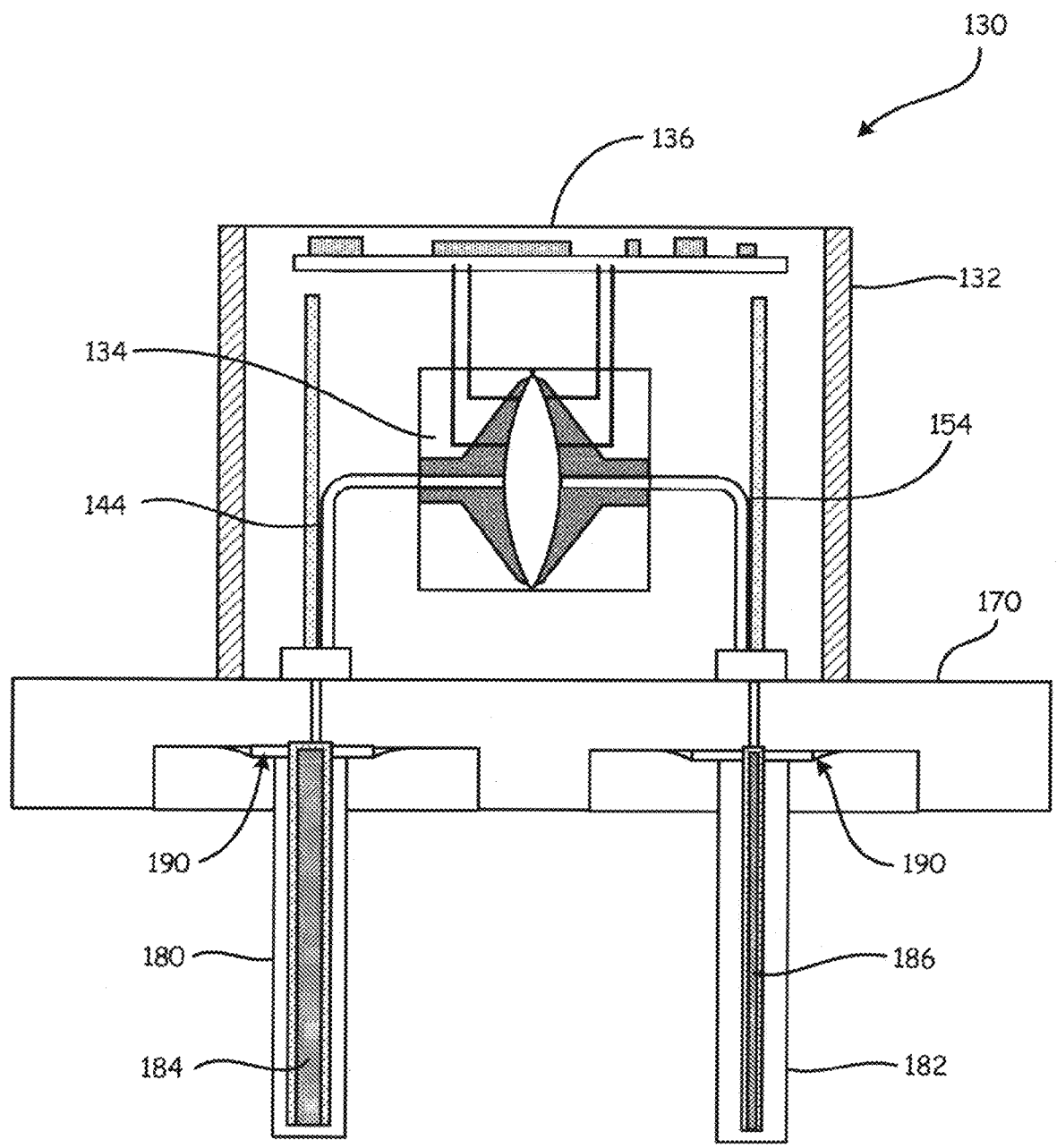
FIG. 5 is a side cross-sectional view of a pressure transmitter coupled to elongated tubes configured to measure corrosion based upon a change in pressure.

FIG. 5 shows another example embodiment of corrosion measurement system 130 using a pressure transmitter 132. In the configuration of FIG. 5, elongated tubes 180, 182 are configured to extend into the process fluid. Tube 180 is a corrosion sensing tube and tube 182 is a reference tube. Tubes 180 and 182 are preferably filled with an insert 184, 186, respectively. The tubes 180, 182 are hollow and filled with a fill fluid which is fluidically coupled to capillary tubes 144, 154. Inserts 184, 186 can be configured to reduce the amount of fill fluid and thereby reduce the temperature effect from volume changes in the fill fluid. Tubes 180, 182 may be of any shape and are not limited to a cylindrical shape.

The outer walls of the tubes 180, 182 act as a type of membrane and deflect under pressure. The thickness of the wall of corrosion sensing tube 180 is less than that of reference tube 182. Thus, if made of the same material, tubes 180, 182 will corrode at the same rate. However, corrosion sensing tube 180 will deflect more in response to the internal pressure as corrosion progresses in comparison to tube 182. This causes tube 180 to be more sensitive to corrosion than tube 182 at a given back pressure. The tubes 180 and 182 may be formed of any appropriate material including, for example, carbon steel. The material used for inserts 184, 186 may be selected as appropriate and may, in some configurations, be configured to expand or contract in a manner which compensates for changes in temperature. The tubes 180, 182 may be welded directly to flange 170 at weld points 190. The fill fluid within tubes 180, 182 may directly couple the fill fluid of capillaries 144, 154, respectively. In another example configuration, isolators may be employed.

Figure 6A:
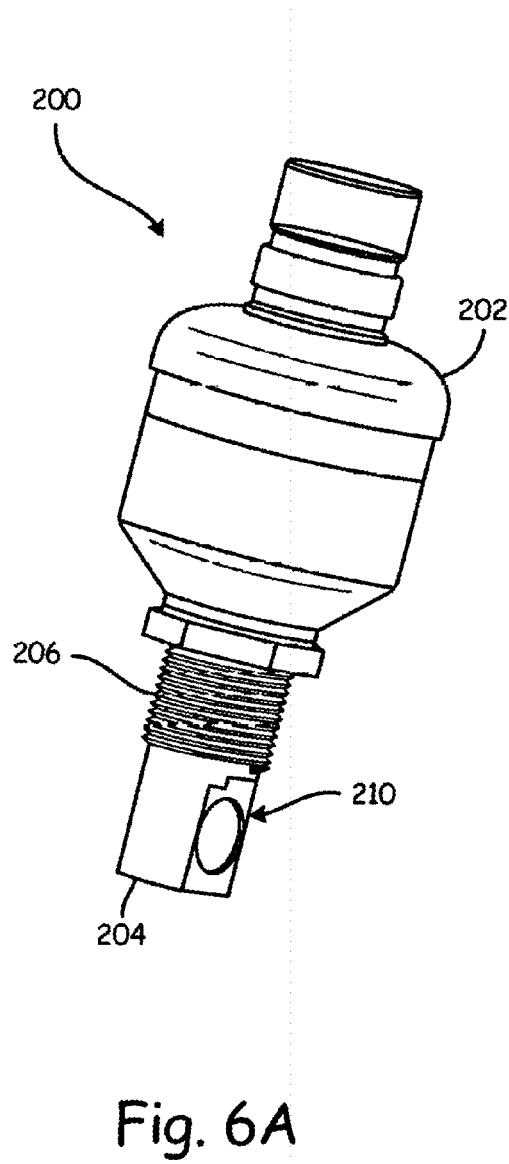
FIG. 6A is a perspective view.
Figure 6B:
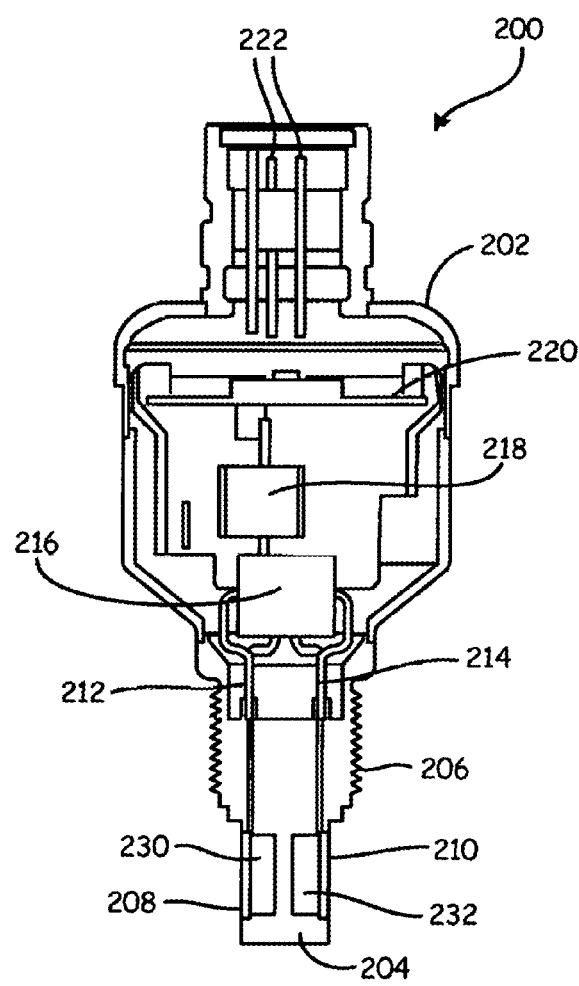
FIG. 6B is a side cross-sectional view and FIG. 6C is a perspective exploded view of a corrosion sensor system formed in a sensing module.
Figures 6C, 6D:
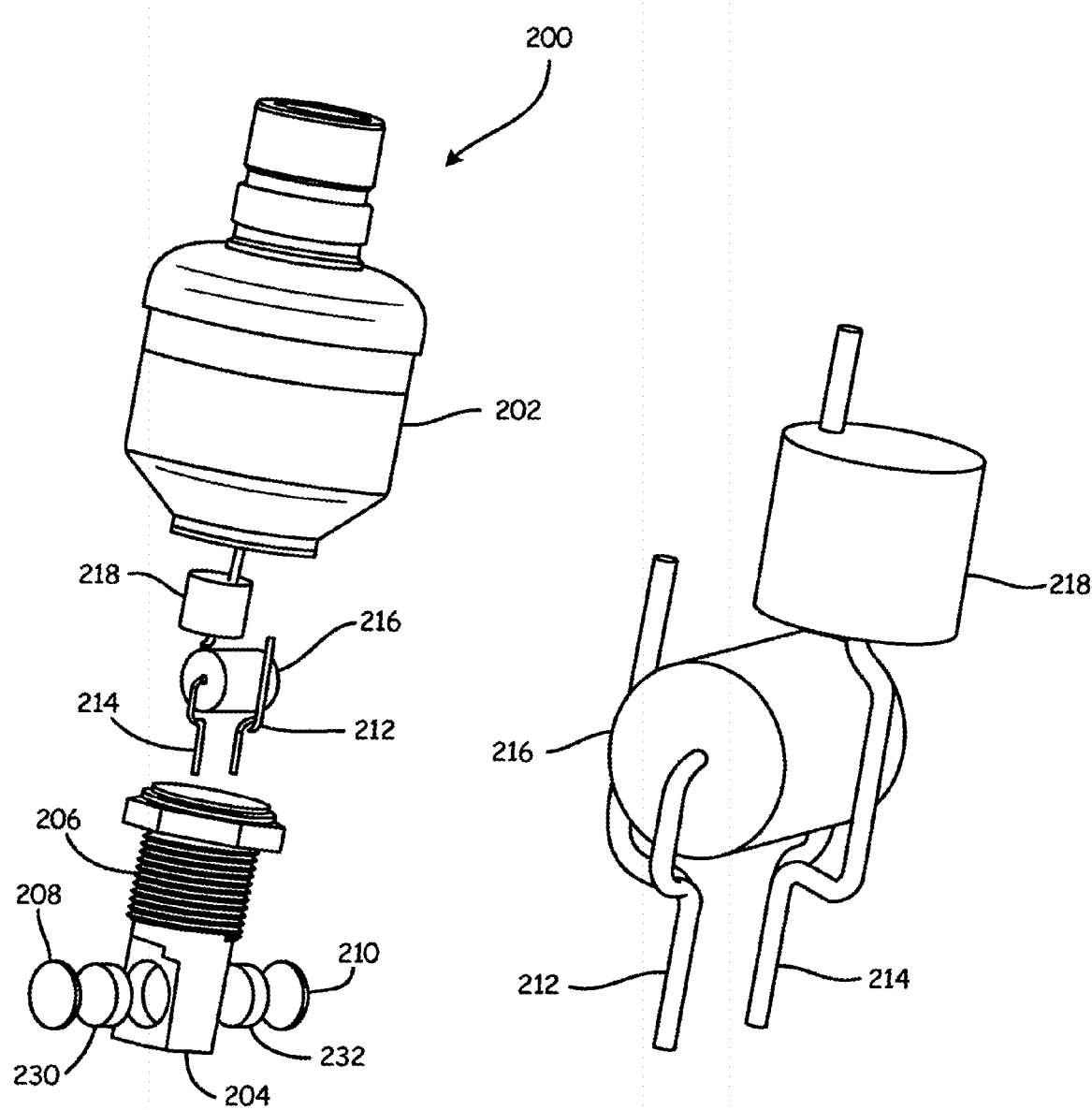
FIG. 6D is a perspective view of sensors used in the module of FIGS. 6A-6C.

FIGS. 6A, 6B, 6C and 6D are views of another example configuration of a corrosion measurement system 200. FIG. 6A is a side perspective view, FIG. 6B is a cross-sectional view and FIG. 6C is an exploded view of the system 200. FIG. 6D is a perspective view of example pressure sensors.

Corrosion measurement system 200 includes a transmitter having a transmitter body 202. A process extension 204 is configured to be mounted to a process vessel, for example process piping, at threading 206. A corrosion sensing (sacrificial) membrane 208 and a reference membrane 210 are carried on extension 204. Pressure applied to membranes 208, 210 is fluidically coupled to pressure sensors 216, 218 through capillary tubes 212 and 214. As can be seen in the embodiment shown in FIG. 6D, sensor 216 receives a differential pressure between capillary tubes 212, 214 whereas sensor 218 only measures a gauge or absolute pressure delivered by capillary tube 214.

Sensors 216 and 218 may be any configuration. In one embodiment, sensors 216, 218 comprise strain gauges having an electrical resistance which changes based upon applied pressure. Measurement circuitry 220 measures an electrical characteristic of sensor 216, 218 related to the applied pressure. As discussed above, this can be correlated to the amount of corrosion of the corrosion sensing membrane 208. Measurement circuitry 220 provides an electrical output 222 related to the sensed pressure, measured corrosion.

A single differential pressure sensor 216 may be employed or two separate gauge or absolute pressure sensors may be used to determine the differential pressure. In the configuration shown in FIG. 6A-D, pressure sensor 218 may be optionally included to measure the internal back pressure of the system. Sensor 218 can be used to compensate for temperature and line pressure effects.

FIGS. 6B and 6C also show quartz disks 230, 232 proximate membranes 208, 210, respectively. Quartz (or other low expansion material) disks 230, 232 may preferably be employed to provide thermal expansion compensation due to expansion of the fill fluid, (such as oil), carried in capillary tubes 212, 214.

Figure 7:
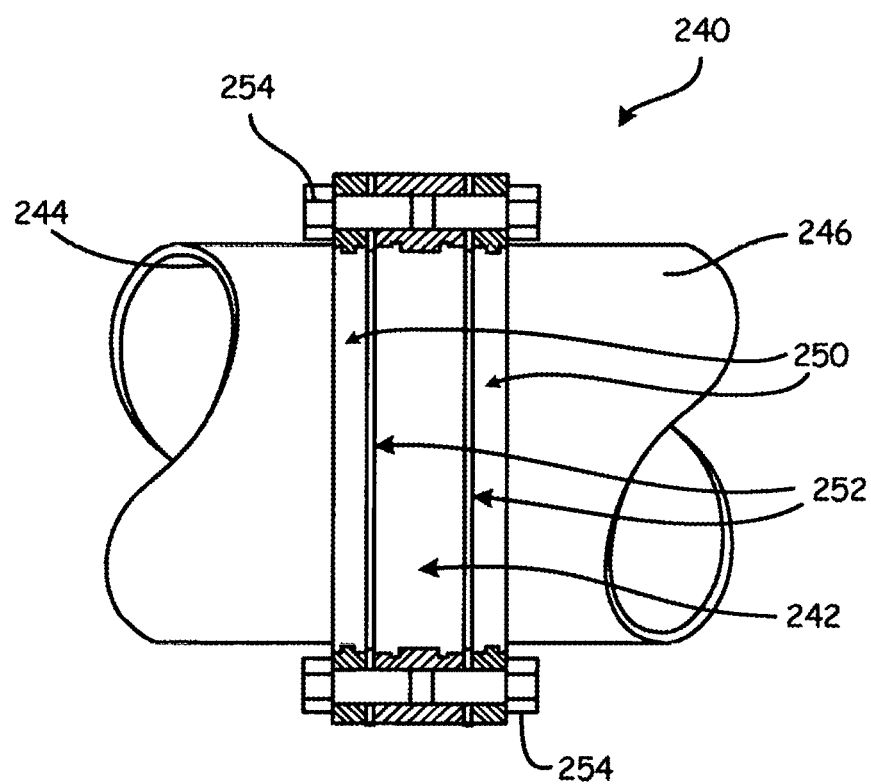
FIG. 7 is a side plan view of a ring insert used for measuring corrosion.
Figure 8:
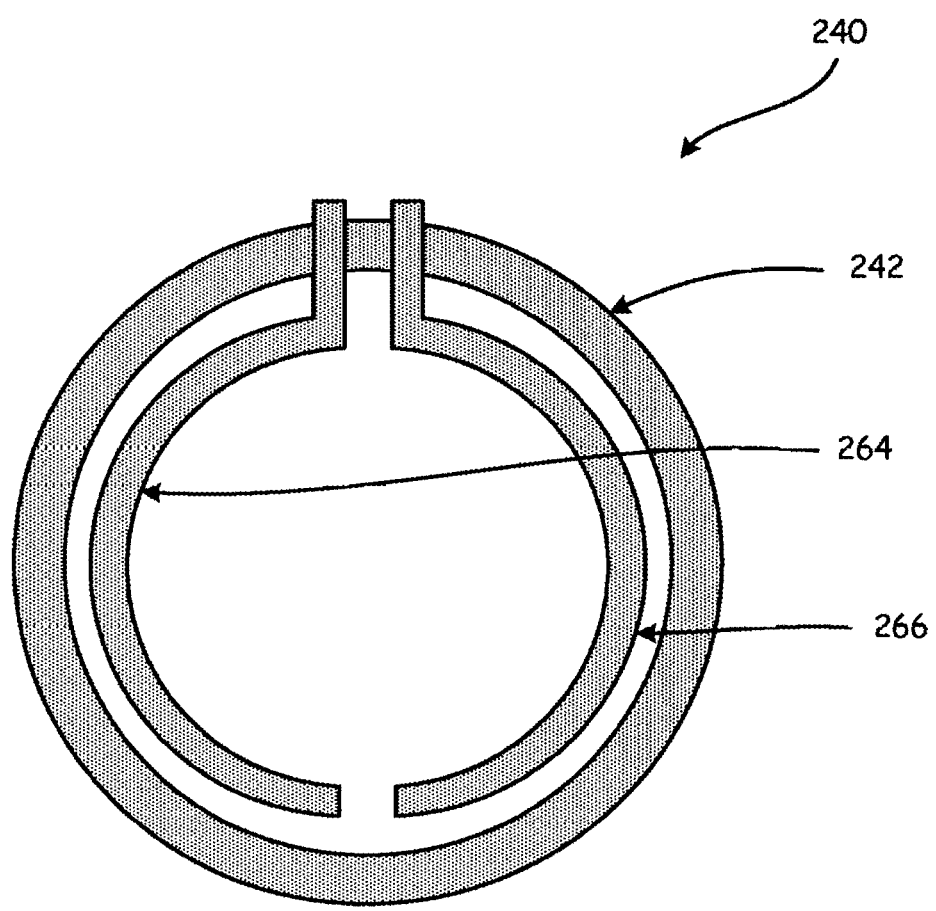
FIG. 8 is a cross-sectional radial view of the ring insert of FIG. 7.

FIGS. 7 and 8 shows another example arrangement of corrosion measurement system 240. FIG. 7 is a side plan view showing a flange ring insert 242 placed between process piping 244 and 246. Process piping 244, 246 includes flanges 250 which are sealed to ring insert 242 with gaskets 252. This allows the device to be inserted into the process utilizing an existing flange seal penetration. This reduces costs and is less intrusive in requiring additional measurement points. Further, it also efficiently enables multivariable measurement and redundant measurement, for example, by adding additional pressure and temperature sensors to the insert 242.

FIG. 8 is a front plan view of system 240 showing tubes which are used to perform corrosion measurement. In FIG. 8, ring insert 242 carries a sacrificial corrosion sensing tube 264 and a reference tube 266. These tubes 264, 266 couple to a pressure transmitter in a manner similar to that discussed in connection with FIG. 5. The ring insert 242 is held between the flanges of process piping as that illustrated in FIG. 7. This configuration allows the measurement of the average corrosion rate of a pipe across the inner circumference of the pipe. For example, the bottom portion of a pipe may corrode at a faster rate if the corrosive fluid is denser than other process fluid.

Although the embodiments shown are specifically designed for the process industry they are applicable to measure corrosion in other industries. For example the device can be used to measure corrosion rates of any steel superstructure such as bridges, buildings, or ships. The sacrificial material would replicate the superstructure material including surface treatments such as paint.

Although the present invention has been described with reference to preferred embodiments, workers skilled in the art will recognize that changes may be made in form and detail without departing from the spirit and scope of the invention. As used herein, a number of different examples of membranes are shown in which one of the membranes changes stiffness due to corrosion at a rate which differs from the other membrane. Deformation of the membrane in response to pressure and/or corrosion is measured and thereby used to measure the rate of corrosion. In some embodiments, the deformation of the membrane causes a cavity to change volume. This change in volume appears as a change in pressure which can be measured by a pressure sensor. Example membranes include a sacrificial coating, a planar element, a tubular element, a bladder or other cavity, as well as a membrane which partially covers another component, such as a sidewall of process piping, etc. Note that the differential pressure sensor could be replaced with dual absolute or gauge pressure sensors such as piezoresistive or sapphire sensors. A differential pressure can be determined by subtracting the signals from the two absolute or gauge pressure sensors.

What is claimed is:

1. A corrosion rate measurement system comprising:
a first membrane of a first material configured to be exposed to a corrosive material and deflect in response to applied pressure and as a function of corrosion;
a second membrane of a second material configured to be exposed to the corrosive material and deflect in response to applied pressure and as a function of corrosion, wherein the second membrane provides a reference for corrosion rate measurement;
a pressure sensor operably coupled to at least one of the first and second membranes through an isolation fill fluid, the pressure sensor configured to measure deflection of at least one of the first and second membranes as a function of a pressure and an amount of corrosion of at least one of the first and second membranes.

2. The corrosion rate measurement system of claim 1, wherein the first and second materials are the same.

3. The corrosion rate measurement system of claim 1, wherein the first and second materials are different.

4. The corrosion rate measurement system of claim 1, wherein the first and second materials have different thicknesses.

5. The corrosion rate measurement system of claim 1, wherein the first and second materials have different surface areas.

6. The corrosion rate measurement system of claim 1, including a first fluid filled conduit which couples the first membrane to the pressure sensor.

7. The corrosion rate measurement system of claim 6, including a second fluid filled conduit which couples the second membrane to the pressure sensor.

8. The corrosion rate measurement system of claim 1, wherein the pressure sensor comprises a differential pressure sensor coupled to the first and second membranes.

9. The corrosion rate measurement system of claim 1, wherein the pressure sensor comprises a first pressure sensor operably coupled to the first membrane and a second pressure sensor operably coupled to the second membrane.

10. The corrosion rate measurement system of claim 1, wherein the membrane comprises a sacrificial coating which coats a portion of the pressure sensor.

11. The corrosion rate measurement system of claim 1, wherein the first membrane comprises an elongated tube.

12. The corrosion rate measurement system of claim 11, wherein the second membrane comprises an elongated tube.

13. The corrosion rate measurement system of claim 1, wherein at least one of the first and second membranes comprise a film which at least partially encloses a cavity and wherein a volume of the cavity changes as a function of corrosion.

14. The corrosion rate measurement system of claim 1, wherein the first and second membranes at least partially enclose a respective first and second cavity and wherein volumes of the cavities change as a function of at least one applied pressure and corrosion of the first membrane.

15. The corrosion rate measurement system of claim 1, wherein the pressure sensor provides an output related to a capacitance which changes as a function of applied pressure.

16. The corrosion rate measurement system of claim 1, wherein an internal back pressure is applied to at least one of the first and second membranes.

17. The corrosion rate measurement system of claim 1, wherein the first membrane is carried in a remote seal spaced apart from the pressure sensor.

18. The corrosion rate measurement system of claim 1, including a housing and wherein the first membrane is carried in the housing.

19. The corrosion rate measurement system of claim 1, wherein the first and second membranes are carried in a ring insert adapted to be mounted between flanges of process piping.

20. The corrosion rate measurement system of claim 1, including a process extension which is configured to extend into the process fluid and wherein the first and second membranes are carried on the process extension.

21. The corrosion rate measurement system of claim 1, wherein the pressure sensor comprises a strain gauge sensor.

22. The corrosion rate measurement system of claim 1, wherein the pressure sensor has an electrical resistance which changes based upon applied pressure.

23. A corrosion rate measurement system comprising:
a first membrane of a first material configured to be exposed to a corrosive material and deflect in response to corrosion;
a second membrane of a second material configured to be exposed to the corrosive material and deflect in response to corrosion, wherein the second membrane provides a reference for corrosion rate measurement;
a pressure sensor operably coupled to at least one of the first and second membranes configured to measure deflection of at least one of the first and second membranes as a function of a pressure and an amount of corrosion of at least one of the first and second membranes;
wherein the membranes comprise a sacrificial coating which coats a portion of the pressure sensor.

* * * * *